US006177538B1

(12) United States Patent
Hesse et al.

(10) Patent No.: US 6,177,538 B1
(45) Date of Patent: Jan. 23, 2001

(54) METHOD FOR PRODUCING TETRABUTYL AMMONIUM PHENOLATE DIPHENOL ADDUCT

(75) Inventors: Carsten Hesse, Tönisvorst; Ursula Jansen, Neuss; Johann Rechner, Kempen, all of (DE)

(73) Assignee: Bayer Aktiengesellschaft, Leverkusen (DE)

( * ) Notice: Under 35 U.S.C. 154(b), the term of this patent shall be extended for 0 days.

(21) Appl. No.: 09/446,999

(22) PCT Filed: Jun. 30, 1998

(86) PCT No.: PCT/EP98/03987

§ 371 Date: Dec. 30, 1999

§ 102(e) Date: Dec. 30, 1999

(87) PCT Pub. No.: WO99/02474

PCT Pub. Date: Jan. 21, 1999

(30) Foreign Application Priority Data

Jul. 11, 1997 (DE) .............................. 197 30 022

(51) Int. Cl.[7] .................................. C08G 65/38
(52) U.S. Cl. ............................ 528/219; 528/86; 528/486; 528/490; 502/164
(58) Field of Search ............................. 528/219, 86, 486, 528/490; 502/164

(56) References Cited

U.S. PATENT DOCUMENTS

| 3,833,572 | 9/1974 | Clark et al. ....................... 260/243 C |
| 4,830,785 | 5/1989 | Shinozaki et al. .................. 252/62.2 |
| 4,939,112 | 7/1990 | Bennett ................................ 502/164 |

OTHER PUBLICATIONS

Journal of the American Chem. Soc., vol. 5, Feb. 9, 1983, pp. 475–483, Mascharak et al.

Single Cubane–Type $MFe_3S_4$ Clusters (M=Mo, W): Synthesis and Properties of Oxidized and Reduced Forms and the Structure of $Et_4N)_3[MoFe_3S_4(S-p-C_6H_4Cl)_4(3,6-(C_3H_5)_2C_6H_2O_2)]$.

Inorganic Chemistry, vol. 24, Oct.–Dec. 1985, pp. 3465–3468, McNeese et al.

Synthesis and characterization of Polynuclear Chromium Carbonyl Tetraanions.

*Primary Examiner*—Duc Truong
(74) *Attorney, Agent, or Firm*—Joseph C. Gil; Aron Preis

(57) ABSTRACT

The invention relates to a method for producing and purifying tetrabutyl ammonium phenolate diphenol adduct by reacting an alkali phenolate with tetrabutyl ammonium salts in an aqueous phase and subsequently precipitating the adduct by adding phenol.

4 Claims, No Drawings

METHOD FOR PRODUCING TETRABUTYL AMMONIUM PHENOLATE DIPHENOL ADDUCT

The invention relates to a process for the production and purification of tetrabutylammonium phenolate diphenol adduct by reaction of alkali phenolate with tetrabutylammonium salts in the aqueous phase and subsequent precipitation of the adduct by addition of phenol.

Tetraalkylammonium phenolates have already become known on several occasions. For instance, J. Am. Chem. Soc. 103 (1983) 475 and Inorg. Chem. 24 (1985) 3465 disclose the production of tetraethylammonium phenolate, the preparation of tetrabutylammonium phenolate is known from DE-OS 22 03 448, EP-A 244 799 teaches the production of an electrolyte containing tetraalkylammonium phenolates.

Various phenol adducts of tetraalkylammonium phenolates have also already become known. J. Chem. Soc. Faraday Trans. 89 (1993) 119 discloses the production of (mono)phenol adducts of various tetrabutylammonium phenolates, and the production of the di(p-tert.-butylphenol) adduct of tetrabutylammonium(p-tert.-butylphenolate) emerges from EP-A 362 854.

Tetrahedron Lett. 3 (1982) 607 discloses a way of producing tetrabutylammonium phenolate diphenol adduct by reaction of tetrabutylammonium hydroxide with phenol in aqueous solution. However, the use of the expensive tetrabutylammonium hydroxide is unsatisfactory for industrial production. A cost-effective process was therefore sought that can be implemented on a technical scale and that results in a product having a low content of alkali ions.

A subject of the invention is a process for the production of tetrabutylammonium phenolate diphenol adduct $N(C_4H_9)_4OC_6H_5*2C_6H_5OH$, wherein, in a first step, alkali phenolate is caused to react with stoichiometric quantities of tetrabutylammonium salt in aqueous phase and, in a second step, two equivalents of phenol are added to the reaction mixture and the adduct is precipitated out.

In a preferred embodiment, in a third step the precipitate that is formed is then separated and washed with water until a sodium content of <1,500 ppm in the precipitate is attained.

In another preferred embodiment, in a third step the reaction mixture is extracted with an organic solvent, the organic phase is separated and freed from solvent.

The alkali phenolates are caused to react in aqueous phase with tetrabutylammonium salts. These tetrabutylammonium salts are preferably salts of monovalent cations such as fluoride, chloride, bromide, iodide, tetrafluoroborate, perchlorate, hexafluorophosphate. For reasons of economy the use of tetrabutylammonium bromide is particularly preferred.

Alkali salt and tetrabutylammonium salt are expediently caused to react in equimolar quantities. Of course, one of the components may also be employed in excess. However, this reduces the yield and impairs the economy of the process.

When implementing the process according to the invention, firstly aqueous solutions of the alkali phenolate and of the tetrabutylammonium salt will preferably be produced and then combined. As a rule, the salt concentration of the initial solutions will amount to about 0.6 to 1.3 mol/l. But it is also possible to dissolve one component in water and then to add the second in solid form. The reaction solution is preferably cooled during the reaction, so that the temperature of the solution does not significantly exceed room temperature.

In the second step of the process, two equivalents of phenol are added to the reaction mixture. Of course, it is also possible to deviate from the exact stoichiometry; but this has a disadvantageous effect on the yield or the purity of the product. The phenol is preferably added slowly in a dropwise manner to the reaction mixture, preferably within about one to two hours, taking care to ensure that reaction mixture and phenol are mixed well. The complex salt $N(C_4H_9)_4OC_6H_5*2C_6H_5OH$ separates out from the reaction mixture. In order to complete the reaction, stirring is preferably continued for a further period of about 60 to 120 minutes.

In a preferred embodiment the precipitate that is formed is then separated. This can be effected by means of the conventional methods known to a person skilled in the art, for example by filtration, sedimentation or centrifugation. The precipitate is then washed with water until a sodium content of <1500 ppm, preferably <750 ppm and in particular <500 ppm, in the precipitate is attained. Hence use of the product also becomes possible in processes that react sensitively to the presence of alkali ions. The product obtained is advantageously subsequently dried. In the course of drying, a temperature below the melting-point of the compound is preferably chosen.

In another preferred embodiment, in a third step the reaction mixture is extracted with an organic solvent, the organic phase is separated and freed from the solvent. By way of extracting agent use is preferably made of halogenated hydrocarbons, methylene chloride being particularly preferred. After the separation of the organic phase the latter is preferably washed with water, in order to remove residues of water-soluble impurities. The organic phase is subsequently freed from solvent in a manner known to a person skilled in the art, for example by distillation under reduced pressure. With this process a product is obtained having a particularly low sodium content. The latter lies, as a rule, below the detection limit, that is to say, around values of <1 ppm.

The diphenol adduct of tetrabutylammonium phenolate produced by the process according to the invention is suitable in particular as a constituent of catalyst systems such as find application, for example, in the production of phenol resins. Also a subject of the invention, therefore, is the use of $N(C_4H_9)_4OC_6H_5*2C_6H_2OH$ as catalyst constituent.

EXAMPLES

Example 1

In a 6000-ml three-neck flask with built-in baffle, precision-glass stirrer, heatable dropping funnel and reflux condenser 510.6 g (3.0 mol) sodium phenolate trihydrate were dissolved in 1800 ml distilled water (Solution A). In a 3 l glass beaker 967.20 g (3.0 mol) tetrabutylammonium bromide were dissolved in 1800 ml distilled water (Solution B).

Subject to cooling, Solution B was then added to Solution A. Subsequently, subject to vigorous stirring, 535.8 g (5.7 mol) phenol were added dropwise during a period of 120 min and stirred for a further period of 120 min. The precipitate that was formed was extracted by suction and washed with 30 l distilled water. The filter residue was dried in a vacuum drying chamber.

Yield: 1147 g (73% of theoretical value) Na content of the dried solid: 570 ppm

Example 2

Example 1 was repeated. Only sodium phenolate was produced in situ by dissolution of 120.0 g (3.0 mol) NaOH in 1800 ml distilled water and addition of 282.3 g (3.0 mol) molten phenol, subject to cooling.

Yield: 1028 g (65% of theoretical value) Na content of the dried solid: 430 ppm

Example 3

In a 500 ml three-neck flask with built-in baffle, precision-glass stirrer, heatable dropping funnel and reflux condenser 113.5 g (0.18 mol) of a 40% solution of tetrabutylammonium hydroxide were diluted with 72 ml distilled water. Subsequently 49.4 g (0.53 mol) phenol were added dropwise within 60 min and stirred for a further period of 60 min. The precipitate was extracted by suction, washed with a little water and then dried in a vacuum drying chamber until the weight was constant.

Yield: 71 g (77% of theoretical value) Na content of the dried solid: ca. 3 ppm

Example 4

In a 500 ml three-neck flask with built-in baffle, precision-glass stirrer, heatable dropping funnel and reflux condenser 29.8 g (0.18 mol) sodium phenolate were dissolved in 80 ml distilled water (Solution A). In a 250 ml glass beaker 48.6 g (0.18 mol) tetrabutylammonium chloride were dissolved in 200 ml distilled water (Solution B).

Subject to cooling, Solution B was added to Solution A. Subject to vigorous stirring, 32.9 g (0.35 mol) phenol were subsequently added dropwise within 60 min; after the addition was completed, stirring was effected for a further period of 60 min. The precipitate that was formed was extracted by suction, washed with water and subsequently dried in a vacuum drying chamber.

Yield: 66.2 g (72% of theoretical value) Na content of the dried solid: 250 ppm

Example 5

In a 2 l three-neck flask with built-in baffle, precision-glass stirrer, heatable dropping funnel and reflux condenser 1 mol sodium phenolate was produced in 500 ml distilled water (Solution A) by dissolution of 40.0 g (1.0 mol) sodium hydroxide in 500 ml water and addition of 94.1 g (1.0 mol) phenol.

In a 2 l glass beaker 322.4 g (1.0 mol) tetrabutylammonium bromide were dissolved in 700 ml distilled water (Solution B).

Solution B was added to Solution A. Subject to vigorous stirring, 188.2 g (2 mol) phenol were added dropwise during a period of 60 min. The resulting suspension was stirred for a further period of 60 min. Extraction with 200 ml methylene chloride was subsequently performed three times. The combined organic phases were washed once with 150 ml water, concentrated using a rotary evaporator and finally dried with the aid of an oil pump. A solid crystal cake was formed.

Yield: 514.0 g (98% of theoretical value) Na content of the solid: <1 ppm

The bromide content was around 3.8 wt-%, which corresponds, reckoned as tetrabutylammonium bromide, to a content amounting to 15.3 wt-%.

Example 6

In a 100-l agitator vessel made of enamel with cooling-water port, distillation head, vacuum/nitrogen port and heatable metering tank 19.7 kg (61.6 mol) tetrabutylammonium bromide were dissolved with 30.5 l fully demineralised water and, with a view to interim storage, filled into a vat lined with Valenthene (Solution A).

In an analogous apparatus 1.22 kg (30.5 mol) NaOH were dissolved in 15.3 kg fully demineralised water and the solution was mixed with 2.83 kg (30.1 mol) molten phenol (Solution B).

Subsequently 25 kg of Solution A (=30.5 mol tetrabutylammonium bromide) were pumped in and mixed well. From the heatable dropping funnel 5.6 kg (59.5 mol) phenol were then added dropwise at room temperature within 140 min, subject to good intermixing. Stirring was effected for a further period of 90 min and subsequently filtration was effected via a large suction filter covered with a Dralon cloth. After washing had been carried out with water, the residue was dried on metal sheets in a vacuum drying chamber at 25° C. until the weight was constant.

Yield: 10.1 kg (63% of theoretical value) Na content: 150 ppm; bromide content: 0.12 wt-%; water content: 400 ppm

Example 7 (Comparative Example)

In a 250 ml glass beaker 8.1 g (0.09 mol) phenol were dissolved in 100 ml water. In a 100 ml glass beaker 55 ml of a 40% solution of tetrabutylammonium hydroxide (=0.085 mol) were diluted with 25 ml distilled water. Both solutions were combined in a shaking funnel, mixed well for about 5 min and the phases were separated. The organic phase was dried over $MgSO_4$ and, after filtration, was concentrated by evaporation. The viscous residue was taken up in 11 ml ethyl acetate. However, it was not possible to isolate a crystalline product from the solution. Even the addition of seed crystals at about 0° C. did not result in crystallisation.

What is claimed is:

1. Process for the production of tetrabutylammonium phenolate diphenol adduct, wherein, in a first step, alkali phenolate is caused to react with stoichiometric quantities of tetrabutylammonium salt in the aqueous phase and, in a second step, two equivalents of phenol are added to the reaction mixture and the adduct is precipitated out.

2. Process according to claim 1, wherein, in a third step, the precipitate that is formed is separated and washed with water until a sodium content of <1,500 ppm in the precipitate is attained.

3. Process according to claim 1, wherein, in a third step, the reaction mixture is extracted with an organic solvent, the organic phase is separated and freed from solvent.

4. A method of using tetrabutylammonium phenolate diphenol adduct as catalyst constituent.

* * * * *